US006624626B2

(12) United States Patent
Khalfin

(10) Patent No.: US 6,624,626 B2
(45) Date of Patent: Sep. 23, 2003

(54) METHOD AND APPARATUS FOR ELECTROMAGNETIC POSITION AND ORIENTATION TRACKING WITH DISTORTION COMPENSATION EMPLOYING MODULATED SIGNAL

(75) Inventor: Igor Khalfin, South Burlington, VT (US)

(73) Assignee: Polhemus Inc., Colchester, VT (US)

( * ) Notice: Subject to any disclaimer, the term of this patent is extended or adjusted under 35 U.S.C. 154(b) by 0 days.

(21) Appl. No.: 10/164,081

(22) Filed: Jun. 4, 2002

(65) Prior Publication Data

US 2003/0016006 A1 Jan. 23, 2003

Related U.S. Application Data

(63) Continuation-in-part of application No. 09/430,978, filed on Nov. 1, 1999, now Pat. No. 6,400,139.
(60) Provisional application No. 60/377,918, filed on May 2, 2002.

(51) Int. Cl.[7] ................................................ G01B 7/14
(52) U.S. Cl. ........................ 324/207.17; 324/207.12; 702/150
(58) Field of Search ................. 324/207.17, 207.12, 324/207.14, 207.15, 207.16, 207.26; 342/386, 448, 463; 340/979, 686.1; 701/207; 600/424; 702/150

(56) References Cited

U.S. PATENT DOCUMENTS

| 4,314,251 | A | | 2/1982 | Raab ........................... 343/112 |
| 4,737,794 | A | | 4/1988 | Jones ........................... 342/448 |
| 5,453,686 | A | | 9/1995 | Anderson .................... 324/207 |
| 5,645,077 | A | | 7/1997 | Foxlin ........................ 128/774 |
| 5,752,513 | A | | 5/1998 | Acker et al. ................. 128/653 |
| 5,754,049 | A | * | 5/1998 | Howell ........................ 324/326 |
| 5,831,260 | A | | 11/1998 | Hansen ........................ 250/221 |
| 6,369,564 | B1 | | 4/2002 | Khalfin et al. .......... 324/207.17 |
| 6,377,041 | B1 | | 4/2002 | Jones, Jr. et al. ............ 324/244 |
| 6,400,139 | B1 | * | 6/2002 | Khalfin et al. .......... 324/207.17 |
| 6,529,006 | B1 | * | 3/2003 | Hayes ......................... 324/326 |
| 6,539,327 | B1 | * | 3/2003 | Dassot et al. ................ 702/150 |

FOREIGN PATENT DOCUMENTS

EP 0 747 662 A1 6/1996

* cited by examiner

*Primary Examiner*—Jay Patidar
(74) *Attorney, Agent, or Firm*—Gifford, Krass, Groh, Sprinkle, Anderson & Citkowski, PC

(57) ABSTRACT

A modulated signal (e.g., single tone FM or AM) and DSP spectral and phase analysis is used to enhance the performance of an AC magnetic tracker. The algorithm allows distinguishing between the direct source—sensor response and the response due to eddy currents, thus allowing elimination of effects of the electromagnetic distortion. This, in turn, eliminates the need for a calibration/mapping, which has proven to be the main obstacle for the wide application of AC electromagnetic tracking systems. The new method and system disclosed do not require witness sensors (but may be used in a combination with them), works in a narrow frequency band that ensures noise stability, may have high operation frequencies (e.g., about 50 kHz) that gives high quality of the signal and increased operation range, as well as high solution update rate, performs real time (each frame) distortion compensation without any prior knowledge about physical properties of distorters. At the same time the new system preserves all known advantages of the AC trackers. The approach finds applicability in head tracking systems and helmet-mounted displays for fighter aircraft, head trackers for armored vehicles, medical-guided surgery and biopsy. The same technology is applicable for remote sensing.

2 Claims, 1 Drawing Sheet

METHOD AND APPARATUS FOR ELECTROMAGNETIC POSITION AND ORIENTATION TRACKING WITH DISTORTION COMPENSATION EMPLOYING MODULATED SIGNAL

REFERENCE TO RELATED APPLICATIONS

This application is a continuation-in-part of U.S. patent application Ser. No. 09/430,978, filed Nov. 1, 1999 now U.S. Pat. No. 6,400,139; and also claims priority from U.S. Provisional Patent Application Ser. No. 60/377,918, filed May 2, 2002. The entire content of each application is incorporated herein by reference.

FIELD OF THE INVENTION

This invention relates generally to AC magnetic tracking systems and, in particular, to the use of a modulate signal in conjunction with distortion compensation.

BACKGROUND OF THE INVENTION

Position and orientation tracking systems (trackers) are well known in the art. They include, for example, AC electromagnetic, inertial, combo—consisting or two different trackers, e.g., optical and magnetic, and others. AC electromagnetic trackers have definite advantages over other kinds: they give highest solution/update rate with high accuracy, not affected by obstructed field of view (versus optical), do not require reference sensor/unit and drift stable (versus inertial), not affected by Earth's magnetic field and ferrous materials (versus DC magnetic). The main disadvantage of AC trackers is their susceptibility to the electromagnetic distortion due to the field of eddy currents induced in the conducting materials in the vicinity of a motion box.

AC Magnetic Tracking systems are very susceptible to distortion due to eddy currents in conductive materials in or near the motion box. To overcome this phenomenon Magnetic Trackers require costly and time-consuming calibration/mapping to be able to function correctly in the distorted environment. The electromagnetic coupling which creates these eddy currents is strongly dependent on the frequency of the transmitted AC magnetic field. In addition, eddy currents are phase shifted with respect to the Magnetic Tracker source drive current that generates the magnetic field.

One of the options to compensate for electromagnetic distortion in AC trackers is mapping, i.e., measurement of the magnetic field profile in the multiple points of the volume of interest (motion box) prior to the actual tracking, see co-owned U.S. Pat. No. 6,377,041 and references therein. While mapping may be done fast and accurately any changes in the motion box will require repeating of the mapping procedure.

Another approach allows the AC tracker to trace moving metal (distortion) by measuring the signal without distortion (acquiring baseline signals) and then comparing this signal with one in the presence of distorting object(s) by measuring the phase error of the received signal. While such a system may work it is not always practical to acquire baseline signal without distortion—in many cases, for example an aircraft cockpit, the distortion is always present.

Yet another approach introduces at least two frequencies per source channel and uses the difference in responses to compensate for the eddy current distortion. This approach requires a guess about the eddy currents loop geometry, and efficiency of the distortion compensation and operation frequencies depends on a kind or distorted environment (guess about physical characteristics of distorting materials) where the system will be working. In addition this approach requires a comparatively wide band receiver (sensor and ADC processing) thus reducing noise stability.

Methods and apparatus for distortion compensated AC tracking described in co-owned patent application Ser. No. 09/430,978 and U.S. Pat. No. 6,369,564, and for wired and wireless sensors use witness sensors to get real time information about distortion, and uses in addition a signal from the resonantly tuned wireless passive sensor phase shifted with respect to the source and distorters.

SUMMARY OF THE INVENTION

The system and method described herein generates a modulated signal (e.g. single tone FM or AM) and performs on the tracker DSP spectral and phase analysis of the signal received by the sensor. The algorithm allows distinguishing between the direct source—sensor response and the response due to eddy currents, thus allowing elimination of effects of the electromagnetic distortion. This, in turn, eliminates the need for a calibration/mapping, which has proven to be the main obstacle for the wide application of AC electromagnetic tracking systems.

The new method and system disclosed below do not require witness sensor (but may be used in a combination with them), works in a narrow frequency band that ensures noise stability, may have high operation frequencies (e.g. about 50 kHz) that gives high quality of the signal and increased operation range, as well as high solution update rate, performs real time (each frame) distortion compensation without any prior knowledge about physical properties of distorters. At the same time the new system preserves all known advantages of the AC trackers.

The approach finds applicability in head tracking systems and helmet-mounted displays for fighter aircraft, head trackers for armored vehicles, medical—guided surgery and biopsy. The same technology is applicable for remote sensing.

DETAILED DESCRIPTION OF THE PREFERRED INVENTION

Figure 1:
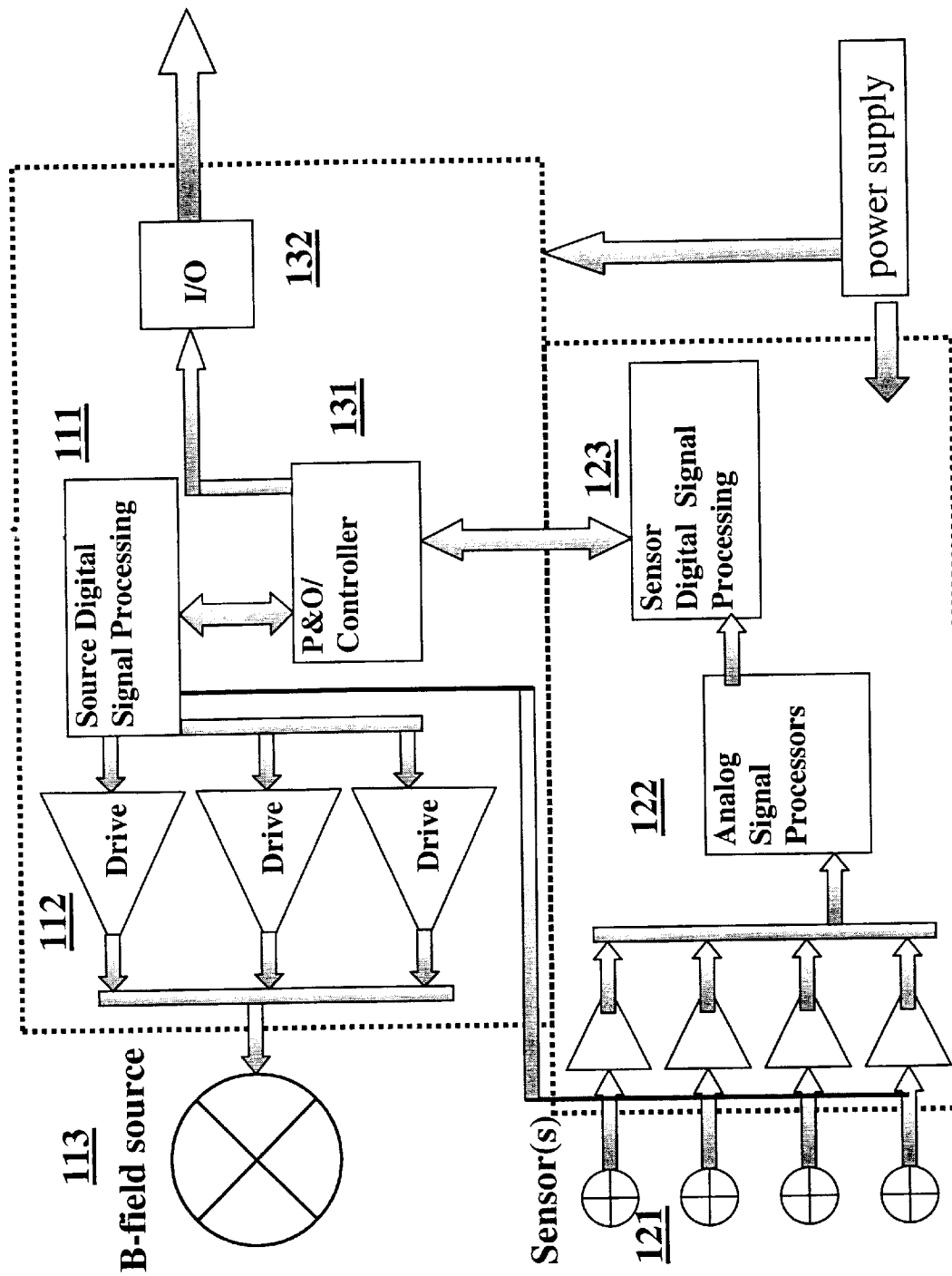
FIG. 1 is a functional diagram of the present invention.

In contrast to prior-art approaches, the system of this invention generates a modulated signal, for example, single tone FM or single tone AM with modulation frequency $f_m$ is much less than the carrier frequency $f_c$.

The system then performs demodulation and spectral analysis of the received signal given well-pronounced symmetry pattern of the carrier-satellites. This allows distinguishing between source-sensor coupling and source-distorter-sensor coupling since each coupling is frequency dependent and has unique phase characteristics. The restored source-sensor response then is plugged into the "free space" solution that is well known in the art.

Another sufficient difference is that the system monitors and stabilizes (either software or hardware) the phase and the magnitude of the source (transmitter) current. Without such a stabilization source drive current may change due to the electromagnetic coupling between the source and conducting materials in a motion box.

The functional diagram of the system is presented on FIG. 1. The source processor 111 generates a composite modulated waveform, that goes to the source drivers 112 and is transmitted by the source 113. The signal is received by the sensor or sensors 121, then demodulated and analyzed by analog and digital signal processors 122 and 123. At this stage the signal is cleansed from the effects of the electromagnetic distortion. The resulting data is transmitted to the "free space" position and orientation computations 131, and the result is output to an external device via I/O controller 132. It should be noted that the system with additional sensors working as "witnesses" might be arranged according to U.S. patent application Ser. No. 09/430,978, thus providing additional distortion and error correction.

The number of coils per sensor and per source may vary from 1 to 3 depending on the number of DOF (degrees of freedom) to be measured. It is preferred to have 3 non-parallel sensor coils and 3 non-parallel source coils for 6 DOF. Consideration regarding number of source/sensor coils versus DOF is well known in the art.

Instead of search coils in the sensors virtually any magnetic flux sensing device may be used, for example, solid state (GMR or PSS), quantum (SQID), or flux gage.

The method of distortion compensation in the case of single tone FM modulation may be illustrated as follows:

Waveform generated by the source drive is:

$$\cos(2\pi f_c t - \alpha \sin(2\pi f_m t)) \qquad (1)$$

This signal has well pronounced components at $f_c - f_m$, $f_c$, and $f_c + f_m$, $f_c >> f_m$.

Sensor receives signal that is time derivative of the source signal multiplied by coupling constant (that contains all sufficient information about position and orientation of the sensor with respect to the source). In a non-distorted environment the data is sampled at 90° behind the source, i.e.—sin DFT (discrete Fourier transform) and, after DFT, satellites and carrier components are:

$$\frac{\alpha}{2} b = S1 \qquad (2a)$$

$$b = S2 \qquad (2b)$$

$$-\frac{\alpha}{2} b = S3, \qquad (2c)$$

where S1, S2, and S3 are sensor responses normalized to the frequencies, b corresponds to the matrix element of the coupling matrix: $\|b\| = \mu\mu_o$ Att $A_{eff}$ D M. All further considerations have a goal to restore S2 in a distorted/scattering environment In the presence of distortion additional term quadratic with respect to the frequency (linear, after normalization) appears with some magnitude a and with the phase shift of the carrier frequency $\phi$, given that we sample data at the zero phase of the non-distorted response. In general, satellites have different phase shifts from the carrier (the difference is proportional to the deviation of frequencies). Note, no information or guess about the values of $\phi$ and a is necessary for further computations.

For the Im part of the acquired signal, e.g. 90° behind the non-distorted source phase we have:

$$-\frac{\alpha}{2} a 2\pi (f_c - f_m)\sin(\varphi - \Delta\varphi) + \frac{\alpha}{2} b = SD1 \qquad (3a)$$

$$-a 2\pi (f_c)\sin(\phi) + b = SD2 \qquad (3b)$$

$$\frac{\alpha}{2} a 2\pi (f_c + f_m)\sin(\varphi + \Delta\varphi) - \frac{\alpha}{2} b = SD3 \qquad (3c)$$

For the Re part we have:

$$-\frac{\alpha}{2} a 2\pi (f_c - f_m)\cos(\varphi - \Delta\varphi) = CD1 \qquad (4a)$$

$$-a\, 2\pi (f_c)\cos(\phi) = CD1 \qquad (4a)$$

$$\frac{\alpha}{2} a 2\pi (f_c + f_m)\cos(\varphi + \Delta\varphi) = CD3 \qquad (4c)$$

Combining terms in equations (3) and (4) and using symmetry of the satellites with respect to the carrier we get:

$$(SD1 + SD3)^2 + (CD1 - CD3)^2 - \alpha^2 CD2^2 = \alpha^2 (SD2 - S2)^2 \frac{f_m^2}{f_c^2} \qquad (5)$$

Taking into account practical consideration that the distortion contribution to the signal is not greater than the direct response and removing the ambiguity of sign we get the answer:

$$S2 = b = \qquad (6)$$

$$\text{sign}(SD2)\left[-\frac{1}{\alpha}\frac{f_c}{f_m}\sqrt{(SD1 + SD3)^2 + (CD1 - CD3)^2 - \alpha^2 CD2^2} + \text{sign}(SD2)SD2\right]$$

Equation (6) defines restored "non-distorted" signal in the presence of distortion.

The values of b from different sensor coils (3 for 6DOF) are sufficient to find position and attitude matrix as it was noted after equation (2).

I claim:

1. In an AC tracking system of the type wherein an electromagnetic field from a source is received by one or more sensors to determine the position and orientation of an object within a volume of interest, a method of minimizing electromagnetic distortion arising from induced eddy currents, comprising the steps of:
    modulating the field;
    demodulating the field detected by the sensors; and
    performing a spectral analysis on the demodulated signal to distinguish between the direct, source-to-sensor response and the response due to the eddy currents; and
    determining the position and orientation of the object in accordance with the direct, source-to-sensor response.

2. The method of claim 1, wherein AM or FM is used to modulate the field.

* * * * *